(12) United States Patent
Yokoi et al.

(10) Patent No.: US 9,180,422 B2
(45) Date of Patent: Nov. 10, 2015

(54) ISOLATOR

(71) Applicant: PANASONIC HEALTHCARE CO., LTD., Toon-shi, Ehime (JP)

(72) Inventors: Yasuhiko Yokoi, Gunma-ken (JP); Koichi Kobayashi, Tochigi-ken (JP); Hiroshi Yamamoto, Osaka-fu (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 13/971,326

(22) Filed: Aug. 20, 2013

(65) Prior Publication Data

US 2013/0336844 A1   Dec. 19, 2013

Related U.S. Application Data

(62) Division of application No. 13/456,588, filed on Apr. 26, 2012, now abandoned.

(30) Foreign Application Priority Data

Apr. 28, 2011   (JP) .................................. 2011-102048

(51) Int. Cl.
| | | |
|---|---|---|
| *A61L 2/20* | (2006.01) | |
| *B01J 19/00* | (2006.01) | |
| *A61L 9/14* | (2006.01) | |
| *C12M 1/12* | (2006.01) | |

(52) U.S. Cl.
CPC ................ *B01J 19/00* (2013.01); *A61L 2/208* (2013.01); *A61L 9/14* (2013.01); *C12M 37/00* (2013.01);
(Continued)

(58) Field of Classification Search
CPC ...................................................... A61L 2/208
USPC ............................................ 422/30, 291, 28
See application file for complete search history.

(56) References Cited

U.S. PATENT DOCUMENTS 4,372,226 A * 2/1983 Erlandsson .................... 110/238
7,186,371 B1 * 3/2007 Watling ............................. 422/3
(Continued)

FOREIGN PATENT DOCUMENTS

| DE | 3523310 A1 | 1/1987 |
|---|---|---|
| EP | 1 886 697 A1 | 2/2008 |

(Continued)

OTHER PUBLICATIONS

English translation of JP 2006-116095 Kawasaki et al. May 2006.*
(Continued)

*Primary Examiner* — Sean E Conley
*Assistant Examiner* — Donald Spamer
(74) *Attorney, Agent, or Firm* — Westerman, Hattori, Daniels & Adrian, LLP

(57) ABSTRACT

An isolator includes: a contamination-target chamber including an inlet and outlet having intake and discharge filters, respectively; and a decontaminating-gas-supply unit to supply decontaminating gas into the chamber without flowing through the filters, the unit including: an atomizer including first and second ports and a nozzle; a first pipe having one and the other ends connected to a compressor and the first port, respectively; a second pipe having one end connected to the second port and the other end open; a reservoir; a pump to take in decontamination solution from the reservoir; and a third pipe, having one end connected to the pump, thorough which the solution flows, the atomizer configured to, when injecting from the nozzle intake air from the first port, suction the solution, via the second pipe, by negative pressure produced in the second port; and inject the solution in an atomized state, mixing it with air.

10 Claims, 10 Drawing Sheets

(52) U.S. Cl.
CPC ........ *A61L 2202/122* (2013.01); *A61L 2202/13* (2013.01); *A61L 2209/14* (2013.01); *A61L 2209/16* (2013.01)

(56) References Cited

U.S. PATENT DOCUMENTS

| | | | | |
|---|---|---|---|---|
| 2001/0032891 | A1* | 10/2001 | Huffman | 239/296 |
| 2007/0098592 | A1 | 5/2007 | Buczynski et al. | |
| 2007/0140893 | A1 | 6/2007 | McVey et al. | |
| 2007/0253859 | A1* | 11/2007 | Hill | 422/3 |
| 2008/0267818 | A1 | 10/2008 | Hill | |
| 2010/0189607 | A1* | 7/2010 | Yokoi et al. | 422/116 |
| 2012/0275965 | A1 | 11/2012 | Yokoi et al. | |
| 2012/0275967 | A1* | 11/2012 | Yokoi et al. | 422/291 |

FOREIGN PATENT DOCUMENTS

| | | | |
|---|---|---|---|
| EP | 2 210 618 A1 | 7/2010 | |
| JP | 2003-339829 A | 12/2003 | |
| JP | 2006-116095 | * 5/2006 | ................ A61L 2/20 |
| JP | 2006-116095 A | 5/2006 | |
| JP | 2010-35832 A | 2/2010 | |
| JP | 2010-51351 A | 3/2010 | |
| JP | 2010-169366 A | 8/2010 | |

OTHER PUBLICATIONS

Extended European Search Report dated Jul. 13, 2012, issued in corresponding European patent application No. 12165615.1.

US Office Action dated Mar. 28, 2013, issued in corresponding U.S. Appl. No. 13/456,588.

US Office Action dated Apr. 11, 2014, issued in corresponding U.S. Appl. No. 13/456,303.

Office Action dated May 8, 2014, issued in U.S. Appl. No. 13/456,588 (19 pages).

Japanese Office Action dated Nov. 18, 2014, issued in corresponding Japanese Application No. 2011-102048. (5 pages).

* cited by examiner

ISOLATOR

CROSS-REFERENCE TO RELATED APPLICATION

This is a divisional application of application Ser. No. 13/456,588 filed on Apr. 26, 2012, which claims the benefit of priority to Japanese Patent Application No. 2011-102048, filed Apr. 28, 2011, of which full contents are incorporated herein by reference.

BACKGROUND OF THE INVENTION

1. Field of the Invention

The present invention relates to an isolator.

2. Description of the Related Art

In an isolator used for work of handling a living-organism-derived material, such as cell culture, it is necessary to provide a dust-free/aseptic environment to the highest degree possible (hereinafter, referred to as aseptic environment) inside a working chamber or a pass box for bringing equipment necessary for the work and the like, in order to prevent intrusion of substances other than those necessary for the work. Hereinafter, a process of killing microorganisms, etc., to realize an aseptic environment is referred to as decontamination, and it is assumed that such a decontamination process includes processes of so-called sterilization, decolonization, and disinfection.

In a sterilizing liquid vaporizing device disclosed in Japanese Laid-Open Patent Publication No. 2003-339829, for example, heated compressed air and hydrogen peroxide solution are mixed and atomized by an atomizer, using hydrogen peroxide as decontamination material which is used for decontamination process, thereby producing hydrogen peroxide gas.

As such, decontaminating gas such as the hydrogen peroxide gas containing decontamination material is produced and supplied into a chamber to be decontaminated, such as a working chamber or a pass box, thereby being able to perform a decontamination process.

Each of an inlet and an outlet of the working chamber or the pass box in the isolator are provided with an air filter such as a HEPA (High Efficiency Particulate Air) filter and a ULPA (Ultra Low Penetration Air) filter, in order to remove impurities, such as dust, contained in gas to be taken in and discharged. However, depending on the combination of the decontaminating gas and the air filter to be used, as in a case where the hydrogen peroxide gas is used as the decontaminating gas and the HEPA filter is used as the air filter, for example, the air filter may have a property of having the decontaminating gas adsorbed thereon easily.

Thus, if the decontaminating gas is supplied from the inlet of the working chamber or the pass box, the decontaminating gas is adsorbed by the air filter, which leads to necessity for supplying more than a necessary amount of the decontaminating gas in expectation of an amount thereof to be absorbed, when decontaminating the working chamber or the pass box, resulting in inefficiency. On the other hand, if the decontaminating gas is supplied to the working chamber or the pass box without an air filter, it is not possible to sufficiently decontaminate the air filter (intake filter) of the inlet.

SUMMARY OF THE INVENTION

An isolator according to an aspect of the present invention, includes: a chamber to be decontaminated including an inlet provided with an intake filter and an outlet provided with a discharge filter; a first flow path through which outside air is taken into the chamber to be decontaminated via the intake filter; a second flow path through which gas in the chamber to be decontaminated is discharged via the discharge filter; a first blower configured to take in the outside air to the chamber to be decontaminated through the first flow path, as well as produce an air current to discharge the gas in the chamber to be decontaminated through the second flow path; a decontaminating gas supply unit configured to supply decontaminating gas into the chamber to be decontaminated without flowing through the intake filter and the discharge filter; a third flow path configured to connect the intake filter and the discharge filter at an exterior of the chamber to be decontaminated; and a second blower configured to produce an air current to circulate the gas in the chamber to be decontaminated through the intake filter, the discharge filter, and the third flow path, when the decontaminating gas is supplied to the chamber to be decontaminated, the decontaminating gas supply unit including: an atomizer including a first port, a second port, and a nozzle; a first pipe having one end connected to an air compressor and another end connected to the first port; a second pipe provided lower than the first port, the second pipe having one end connected to the second port and an other end open; a reservoir portion configured to store decontamination solution; a pump configured to take in decontamination solution from the reservoir portion; and a third pipe, having one end connected to the pump, thorough which the decontamination solution taken in by the pump flows, the atomizer configured to, when injecting from the nozzle air taken in from the first port, suction decontamination solution flowing through the third pipe, via the second pipe, by the negative pressure produced in the second port; and inject the decontamination solution in an atomized state from the nozzle, mixing the decontamination solution with air.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION OF THE INVENTION

At least the following details will become apparent from descriptions of this specification and of the accompanying drawings.

Configuration of Isolator

Description will hereinafter be given of a configuration of an isolator according to an embodiment of the present invention with reference to FIG. 1. In an embodiment of the present invention, it is assumed that decontamination effect is achieved by performing the exposure of space to be decontaminated to hydrogen peroxide gas of a predetermined concentration for a predetermined time period, using hydrogen peroxide as an example of a decontamination material which is used in a decontamination process.

Figure 1:
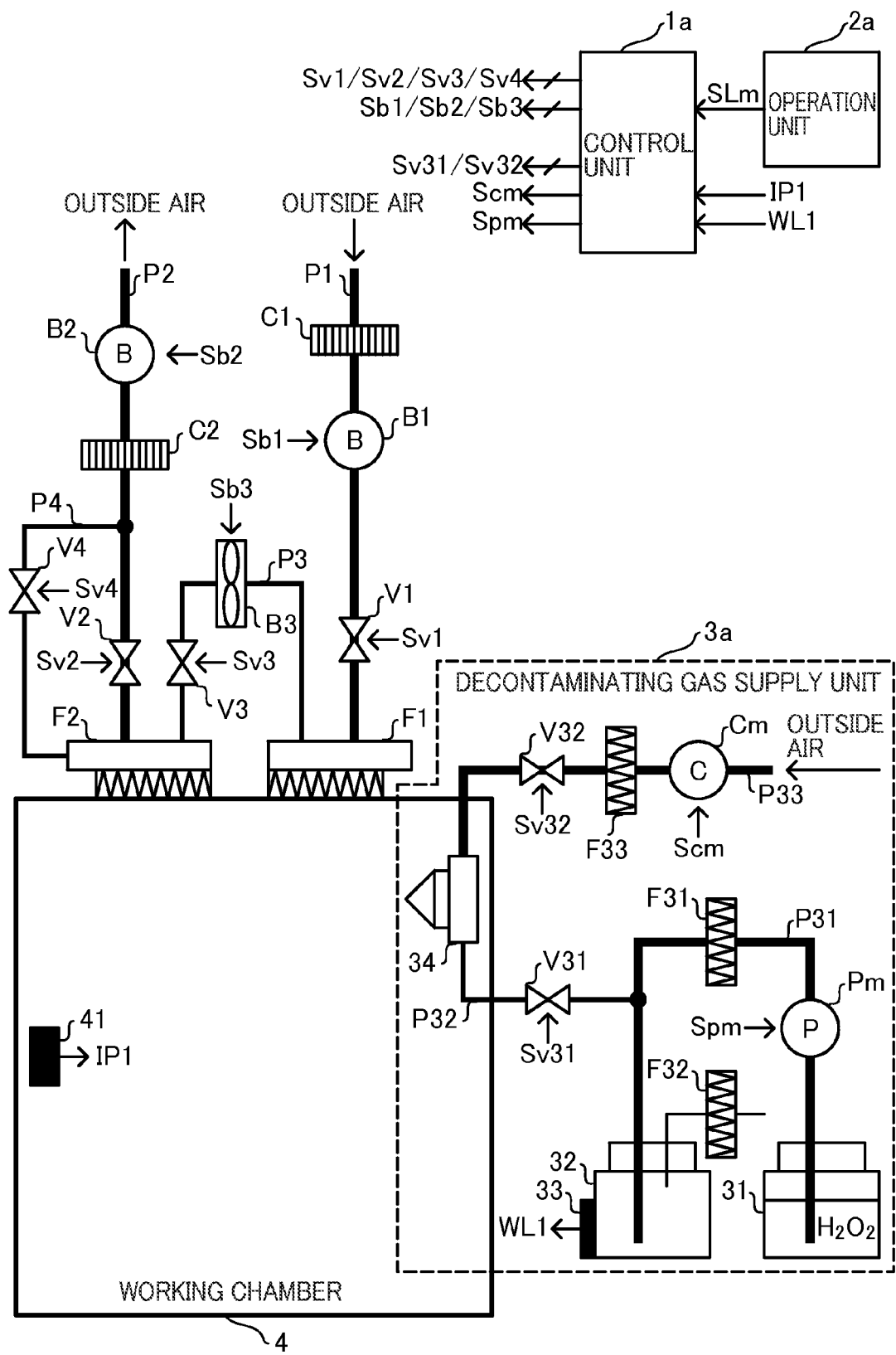
FIG. 1 is a block diagram illustrating a configuration of an isolator according to an embodiment of the present invention.

In the isolator illustrated in FIG. 1, it is assumed that a working chamber 4 for working in an aseptic environment is the chamber to be decontaminated, and the isolator includes a control unit 1*a*, an operating unit 2*a*, and a decontaminating gas supply unit 3*a*. Further, the working chamber 4 includes an inlet provided with an (intake) filter F1 and an outlet provided with a (discharge) filter F2, and the inlet and outlet are provided with flow paths P1 to P4 that are made of pipes, tubes, or the like. Further, the working chamber 4 includes a pressure sensor 41 configured to measure an internal pressure IP1 of the working chamber 4. The filters F1 and F2 are air filters to remove impurities, such as dust, contained in gas to be taken in and discharged, and a HEPA filter is used, for example.

A (first) flow path P1 is a flow path for taking in outside air to the working chamber 4 through the filter F1, and a catalyst C1, a blower (fan) B1, and a (first) valve V1 are provided on the flow path P1. The blower B1 is a centrifugal multi-blade fan, for example, and is configured to produce an air current to take in the outside air to the working chamber 4 through the flow path P1 in response to a control signal Sb1. Such an air current causes the outside air to flow in through the catalyst C1, to be further supplied into the working chamber 4 through the filter F1. The valve V1 is provided between the blower B1 and the filter F1, and is configured to open/close the flow path P1 in response to a control signal Sv1.

A (second) flow path P2 is a flow path for discharging gas in the working chamber 4 through the filter F2, and a blower B2, a catalyst C2, and a (second) valve V2 are provided on the flow path P2. The blower B2 is a centrifugal multi-blade fan, for example, and is configured to produce an air current to discharge the gas in the working chamber 4 through the flow path P2 in response to a control signal Sb2. Such an air current causes the gas in the working chamber 4 to flow out through the filter F2, and the hydrogen peroxide (decontamination material), upon being decomposed/rendered harmless by the catalyst C2, to be discharged to the exterior. In an embodiment of the present invention, the blowers B1 and B2 combined correspond to a first blower for intake/discharge, and the catalyst C2 corresponds to a rendering harmless unit configured to reduce a decontamination material to be rendered harmless. The valve V2 is provided between the catalyst C2 and the filter F2, and is configured to open/close the flow path P2 in response to a control signal Sv2.

A (third) flow path P3 connects the filter F1 and the filter F2 at the exterior of the working chamber 4, and a (second) blower B3 and a (third) valve V3 are provided on the flow path P3. The blower B3 is an axial-flow fan, for example, and is configured to produce an air current to circulate the gas in the working chamber 4 through the filters F1, F2, and the flow path P3 in response to a control signal Sb3 in a decontaminating gas production mode and a decontaminating gas exposure mode which will be described later. Such an air current causes the gas in the working chamber 4 to flow out through either one of the filters F1 and F2, and further through the flow path P3, then to be resupplied into the working chamber 4 through the other filter thereof. The valve V3 is configured to open/close the flow path P3 in response to a control signal Sv3.

A (fourth) flow path P4 is another flow path, different from the flow path P2, for discharging the gas in the working chamber 4 through the filter F2 in the decontaminating gas production mode and the decontaminating gas exposure mode, which will be described later, and generally the flow rate of the gas therein is smaller than that in each of the flow paths P1 and P2. One end of the flow path P4 is connected to the flow path P2 between the catalyst C2 and the valve V2 while the other end thereof is connected to the filter F2, and a (fourth) valve V4 is provided on the flow path P4. The valve V4 is configured to open/close the flow path P4 in response to a control signal Sv4.

The decontaminating gas supply unit 3*a* includes a tank 31, a bottle 32, a water level sensor 33, an atomizer 34, and a filter F32, and further includes flow paths P31 to P33, made of pipes, tubes, or the like, which are provided to connect the above components.

A flow path P31 connects between the tank 31 and the bottle 32, and a pump Pm and a filter F31 are provided on the flow path P31. For example, a peristaltic pump is used as the pump Pm so as to deliver fluid in a state dust-free and aseptic as possible, and hydrogen peroxide solution (decontamination material solution) stored in the tank 31 is taken in, in response to a control signal Spm. Then, the hydrogen peroxide solution taken in as such is delivered toward the atomizer 34 side through the filter F31 for removing impurities, such as dust.

The bottle 32 is opened to the outside air through the (air) filter F32, and acts as a buffer for collecting the hydrogen peroxide solution that has not been injected as hydrogen peroxide gas (decontaminating gas) from the nozzle of the atomizer 34. The bottle 32 is provided with a water level sensor 33 configured to measure water level WL1 of the collected hydrogen peroxide solution.

One end of the flow path P32 is connected between the filter F31 and the bottle 32 in the flow path P31 while the other end thereof is connected to a lower port of the atomizer 34, and a valve V31 is provided on the flow path P32. The valve V31 is configured to open/close the flow path P32 in response to a control signal Sv31.

A flow path P33 is a flow path for supplying compressed air (compressed gas) to the atomizer 34, and a compressor Cm, a filter F33, and a valve V32 are provided on the flow path P33. The compressor Cm is configured to take in the outside air and compress it in response to a control signal Scm, and such compressed air is supplied to an upper port of the atomizer 34 through the (air) filter F33 for removing impurities, such as dust and moisture content. The valve V32 is provided between the filter F33 and the upper port of the atomizer 34 and is configured to open/close the flow path P33 in response to a control signal Sv32.

A mode selection signal SLm is inputted to the control unit 1*a* from the operating unit 2*a*, and the control unit 1*a* is configured to switch the operation mode, which will be described later, in response to the mode selection signal SLm. Further, control unit 1a is configured to output, in addition to switching the operation mode, the control signals Sv1 to Sv4, Sv31, Sv32, Sb1 to Sb3, Scm, and Spm for controlling the valves, blowers, the compressor Cm, and the pump Pm based on the internal pressure IP1 and the water level WL1.

Operation of Isolator

A description will hereinafter be given of an operation of the isolator according to an embodiment of the present invention with reference to FIGS. 2 to 6, as appropriate.

The operation mode of the isolator according to an embodiment of the present invention is switched in response to the mode selection signal SLm, and such mode can be broadly classified into: a decontaminating operation mode (SLm=1 to 4) for decontaminating the working chamber 4 (chamber to be decontaminated); and an aseptic operation mode (SLm=5) for working in the working chamber 4 where the aseptic environment has been provided by decontamination being performed. The decontaminating operation mode includes a leak test mode (SLm=1) the decontaminating gas production mode (SLm=2), the decontaminating gas exposure mode (SLm=3), and a decontaminating gas discharge mode (SLm=4).

Figure 2:
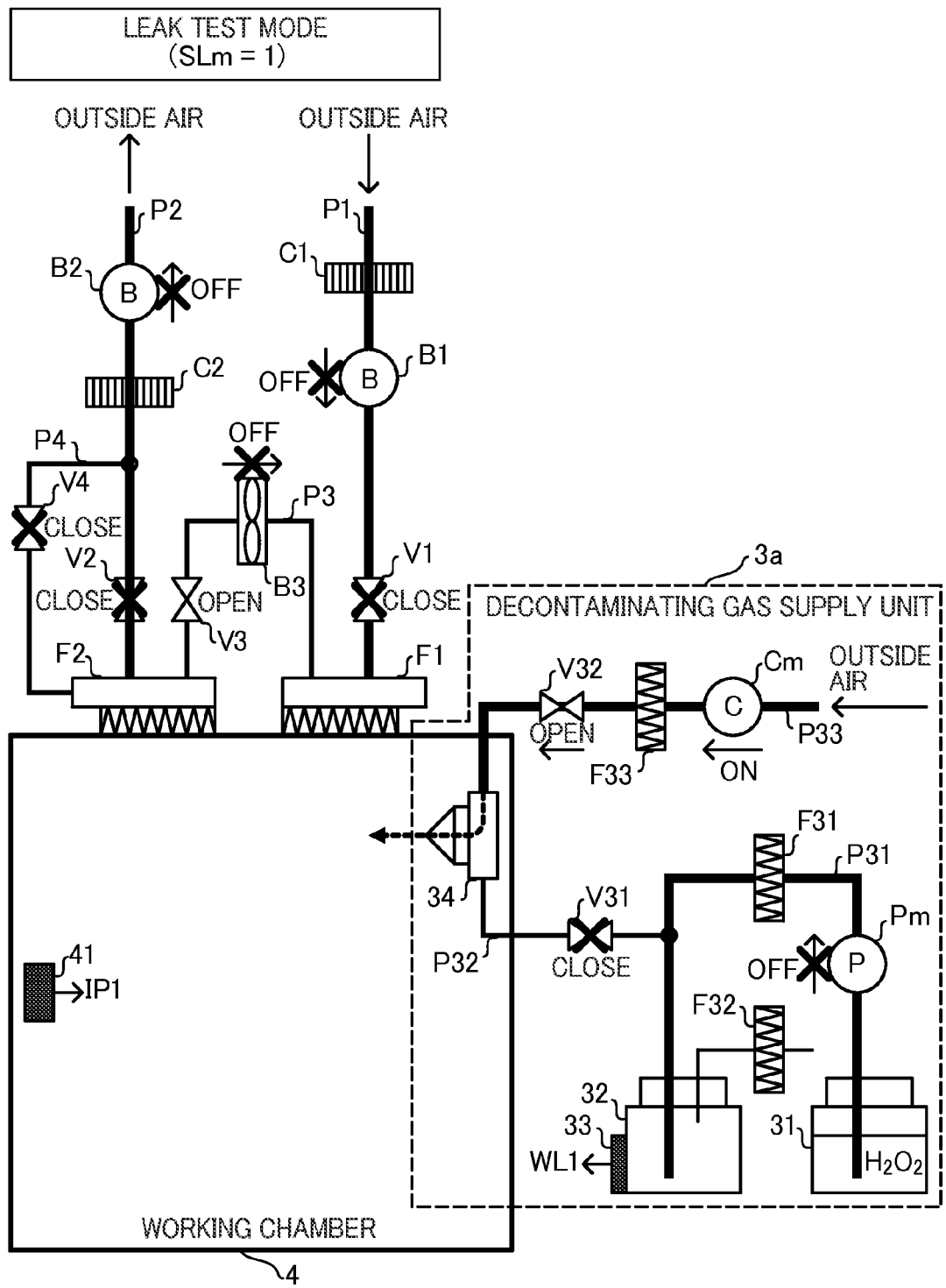
FIG. 2 is a block diagram illustrating states of valves, blowers, a compressor Cm, and a pump Pm in a leak test mode.

In the decontaminating operation mode, firstly, airtightness of the working chamber 4 is tested in the leak test mode. In the leak test mode, as illustrated in FIG. 2, the control unit 1a is configured to drive the compressor Cm as well as open the valve V32 and further open the valve V3 in a state where the blowers B1 to B3 and the pump Pm are stopped with the valves V1, V2, V4, and V31 closed. Then, by such control, the atomizer 34 of the decontaminating gas supply unit 3a supplies, from a nozzle thereof, only the compressed air supplied to the upper port thereof into the working chamber 4, thereby pressurizing the working chamber 4.

In such pressurized state of the working chamber 4, the control unit 1a determines the airtightness of the working chamber 4 based on the internal pressure IP1 of the working chamber 4 measured by the pressure sensor 41. For example, the control unit 1a determines that the airtightness of the working chamber 4 is in a good condition, when an amount of decrease in the internal pressure IP1 after elapse of a predetermined time equals a pressure that is equal to or lower than a predetermined pressure.

In the isolator according to an embodiment of the present invention, it is possible to test the airtightness of not only the working chamber 4 but also the flow path P3 in the leak test mode.

Figure 3:
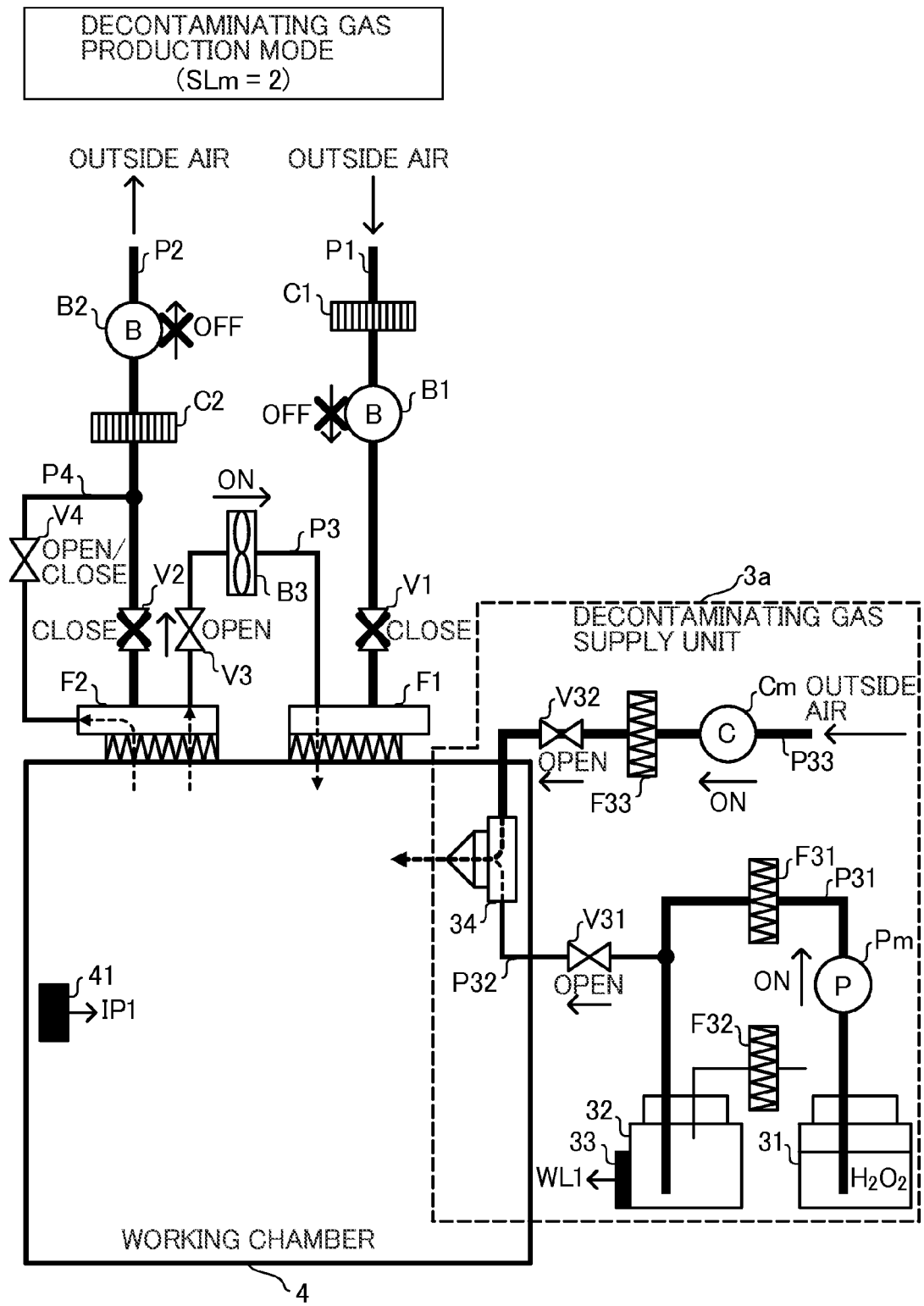
FIG. 3 is a block diagram illustrating states of valves, blowers, a compressor Cm, and a pump Pm in a decontaminating gas production mode.

When it is determined that the airtightness of the working chamber 4 is in a good condition in the leak test mode, next the hydrogen peroxide gas is supplied into the working chamber in the decontaminating gas production mode. The decontaminating gas production mode is commenced, when the control unit 1a drives the pump Pm and opens the valve V31, drives the blower B3 and opens the valve V3, in the state of the leak test mode, and further, controls opening/closing of the valve V4, as illustrated in FIG. 3.

By such control, the compressed air is supplied to the upper port of the atomizer 34, as in the leak test mode. Negative pressure is produced by injecting the compressed air from the nozzle of the atomizer 34, and such negative pressure causes the hydrogen peroxide solution, delivered by the pump Pm from the tank 31 toward the atomizer 34, to be supplied to the lower port of the atomizer 34. Then, the compressed air and the hydrogen peroxide solution are mixed in the atomizer 34, to be injected as atomized hydrogen peroxide solution, thereafter immediately vaporized, and supplied as the hydrogen peroxide gas.

As such, in the isolator according to an embodiment of the present invention, the hydrogen peroxide gas is directly supplied into the working chamber 4 without flowing through the filters F1 and F2, in the decontaminating gas production mode. Thus, the hydrogen peroxide gas is supplied into the working chamber 4 without loss by absorption into the filters F1 and F2, thereby being able to perform a process of decontaminating the inside of the working chamber 4 in an efficient manner.

The decontaminating gas supply unit 3a can produce hydrogen peroxide gas utilizing the negative pressure produced by injection of compressed air, without heating or using ultrasonic waves. If some kind of failure should stop the supply of the compressed air to the atomizer 34, the hydrogen peroxide solution delivered by the pump Pm is collected in the bottle 32 utilizing the difference in flow-path resistance caused by the difference in flow-path diameter, avoiding supply into the working chamber 4 in a liquid state. Then, the control unit 1a stops the pump Pm to stop delivering the hydrogen peroxide solution when the water level WL1 of the hydrogen peroxide solution measured by the water level sensor 33 reaches a water level that is equal to or greater than a predetermined level.

Figure 4:
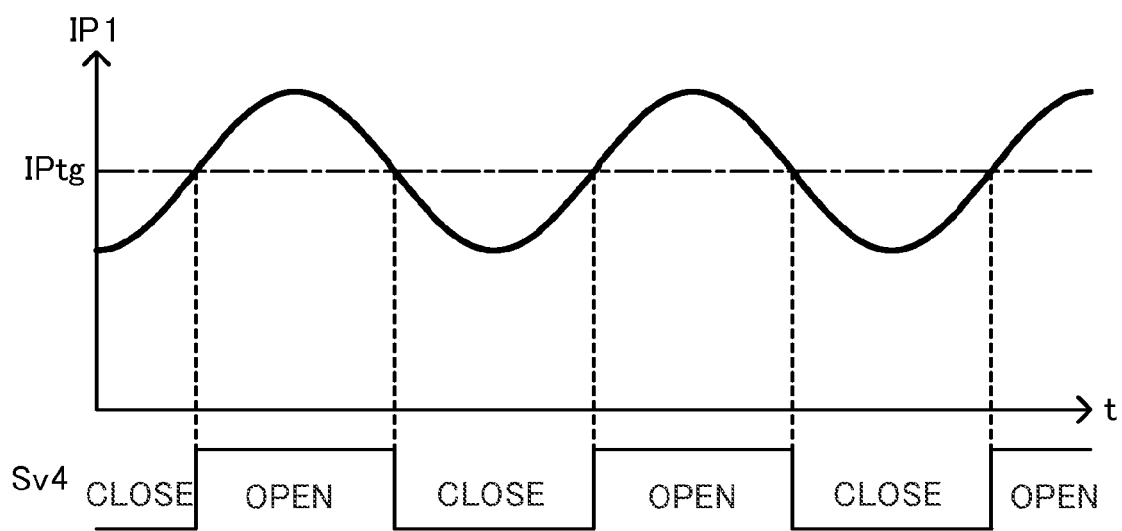
FIG. 4 is a diagram illustrating control of a valve V4 in a decontaminating gas production mode and a decontaminating gas exposure mode.

In the decontaminating gas production mode, the control unit 1a also circulates the hydrogen peroxide gas in the working chamber 4 by the blower B3 from the filter F2 through the flow path P3 toward the filter F1, for example. The direction of the air current to circulate the hydrogen peroxide gas may be the direction opposite the above described direction, and also may be reversed alternately. Further, the control unit 1a controls opening/closing of the valve V4 based on the internal pressure IP1 of the working chamber 4. For example, as illustrated in FIG. 4, when the internal pressure IP1 exceeds a predetermined positive pressure IPtg, the valve V4 is opened; whereas when the internal pressure IP1 equals or falls below the predetermined positive pressure IPtg, the valve V4 is closed.

As such, in the isolator according to an embodiment of the present invention, in the decontaminating gas production mode, the hydrogen peroxide gas in the working chamber 4 is circulated through the filters F1, F2, and the flow path P3, while the internal pressure IP1 of the working chamber 4 is adjusted to the predetermined positive pressure IPtg. Thus, it is possible to sufficiently decontaminate not only the filter F2, which is the discharge filter, but also the filter F1, which is the intake filter.

Figure 5:
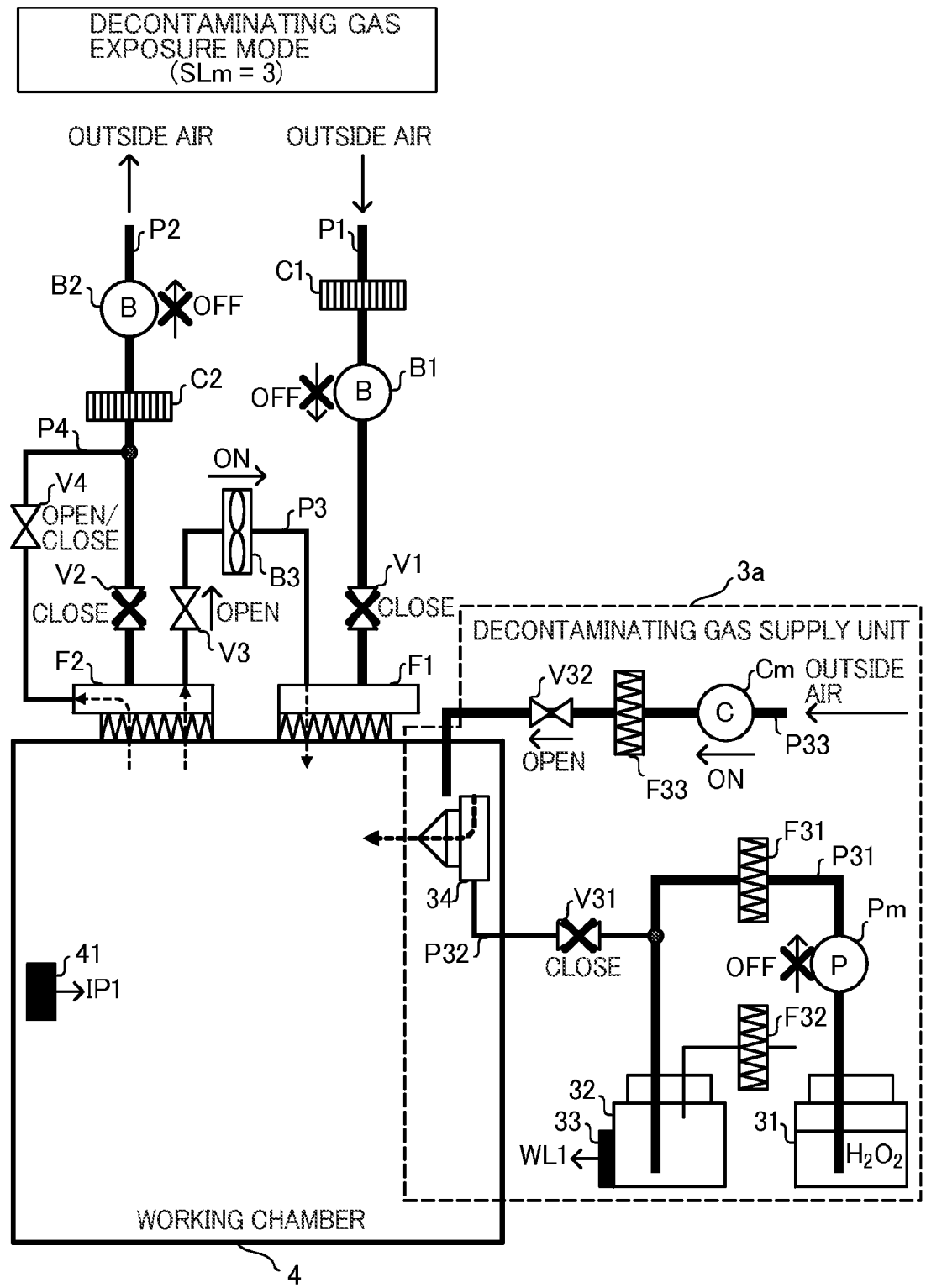
FIG. 5 is a block diagram illustrating states of valves, blowers, a compressor Cm, and a pump Pm in a decontaminating gas exposure mode.

The hydrogen peroxide gas is supplied into the working chamber 4 in the decontaminating gas production mode, and thereafter, the exposure of the interior of the working chamber to the hydrogen peroxide gas is performed in the decontaminating gas exposure mode. In the decontaminating gas exposure mode, from the state of the decontaminating gas production mode, the control unit 1a stops the pump Pm as well as closes the valve V31, as illustrated in FIG. 5. Then, by such control, the decontaminating gas supply unit 3a supplies, from the nozzle, only the compressed air into the working chamber 4 as in the leak test mode, and further, the control unit 1a circulates the hydrogen peroxide gas in the working chamber 4 as well as controls opening/closing of the valve V4 based on the internal pressure IP1 of the working chamber 4 as in the decontaminating gas production mode. The permissible flow rate through the valve V4 is lower than that through each of the valves V1 and V2, which leads the valve V4 to have greater responsiveness, thereby being able to accurately control the internal pressure IP1 with the control unit 1a.

As such, in the isolator according to an embodiment of the present invention, in the decontaminating gas exposure mode, the interior of the working chamber 4 is exposed to the hydrogen peroxide gas, which is supplied in the decontaminating gas production mode. Further, in the decontaminating gas exposure mode as well, the hydrogen peroxide gas in the working chamber 4 is circulated through the filters F1 and F2, and the flow path P3, while the internal pressure IP1 of the working chamber 4 is adjusted to the predetermined positive pressure IPtg. Thus, by shifting from the decontaminating gas production mode to the decontaminating gas exposure mode, the interior of the working chamber 4 and the filters F1 and F2 can be sufficiently decontaminated while suppressing the consumption of the hydrogen peroxide solution stored in the tank 31.

Figure 6:
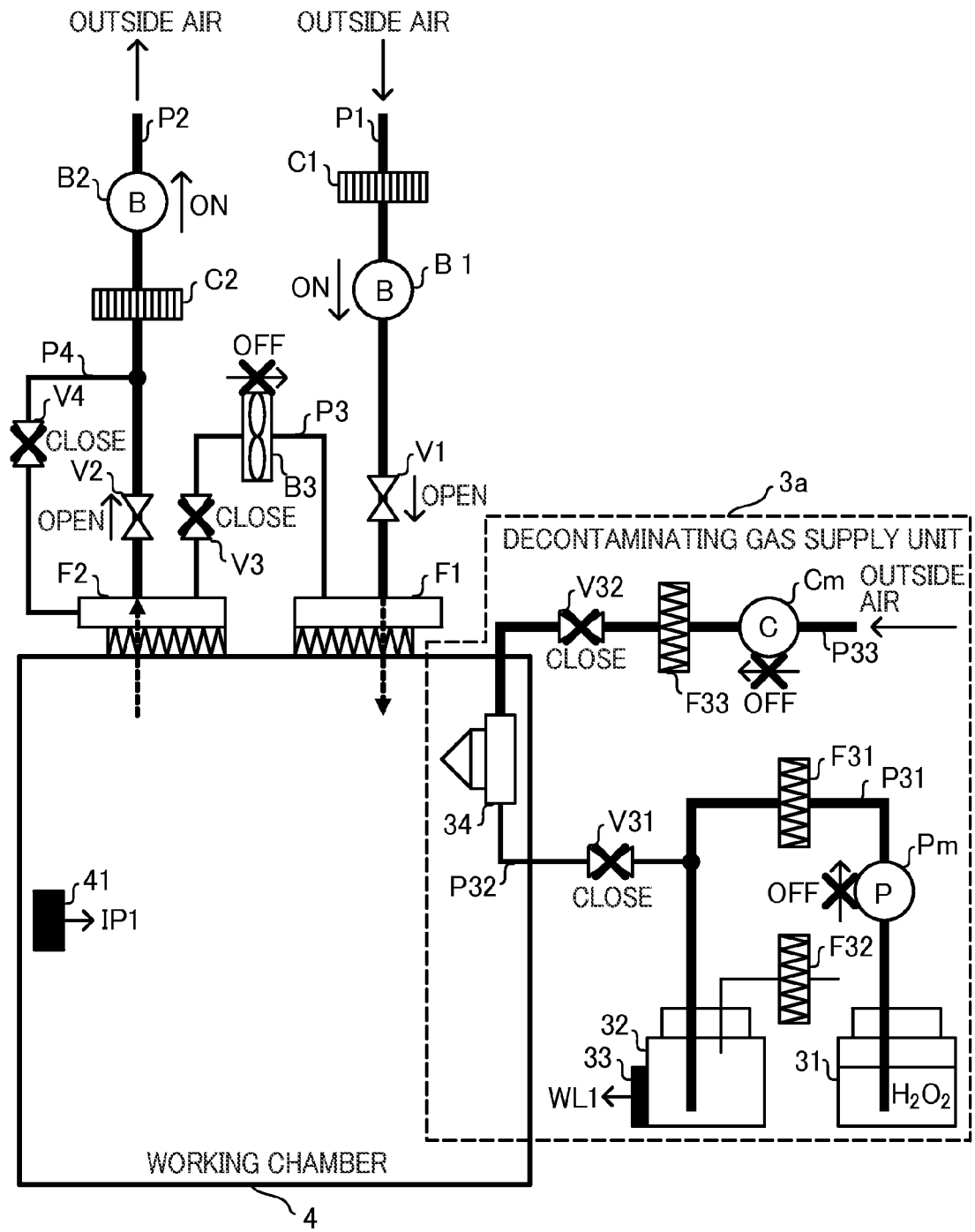
FIG. 6 is a block diagram illustrating states of valves, blowers, a compressor Cm, and a pump Pm in a decontaminating gas discharge mode and an aseptic operation mode.

After the interior of the working chamber 4 is sufficiently exposed to the hydrogen peroxide gas in the decontaminating gas exposure mode, the hydrogen peroxide gas in the working chamber 4 is discharged in the decontaminating gas discharge mode. In the decontaminating gas discharge mode, after proceeding from the state of the decontaminating gas exposure mode, the control unit 1a drives the blowers B1 and B2 as well as opens the valves V1 and V2; stops the blowers B3 as well as closes the valve V3; and stops the compressor Cm as well as closes the valve V32, and further closes the valve V4, as illustrated in FIG. 6.

By such control, the decontaminating gas supply unit 3a stops supplying the compressed air and the hydrogen peroxide gas into the working chamber 4. Further, the control unit 1a controls the number of revolutions of the blowers B1 and B2 based on the internal pressure IP1 of the working chamber 4, and adjusts the internal pressure IP1 of the working chamber 4 to the predetermined positive pressure IPtg, as in the decontaminating gas production mode and the decontaminating gas exposure mode. Thus, the outside air is taken into the working chamber 4 through the flow path P1, and the hydrogen peroxide gas in the working chamber 4 is discharged through the flow path P2. Then, through continuous operation of such for predetermined time period, the hydrogen peroxide gas in the working chamber 4 is replaced by outside fresh air.

In the isolator according to an embodiment of the present invention, the filter F2 is decontaminated in the decontaminating gas discharge mode as well. Further, after the hydrogen peroxide gas in the working chamber 4 is sufficiently discharged in the decontaminating gas discharge mode, the mode proceeds to the aseptic operation mode, and control therein is similar to that in the decontaminating gas discharge mode.

Another Configuration Example of Isolator

Figure 7:
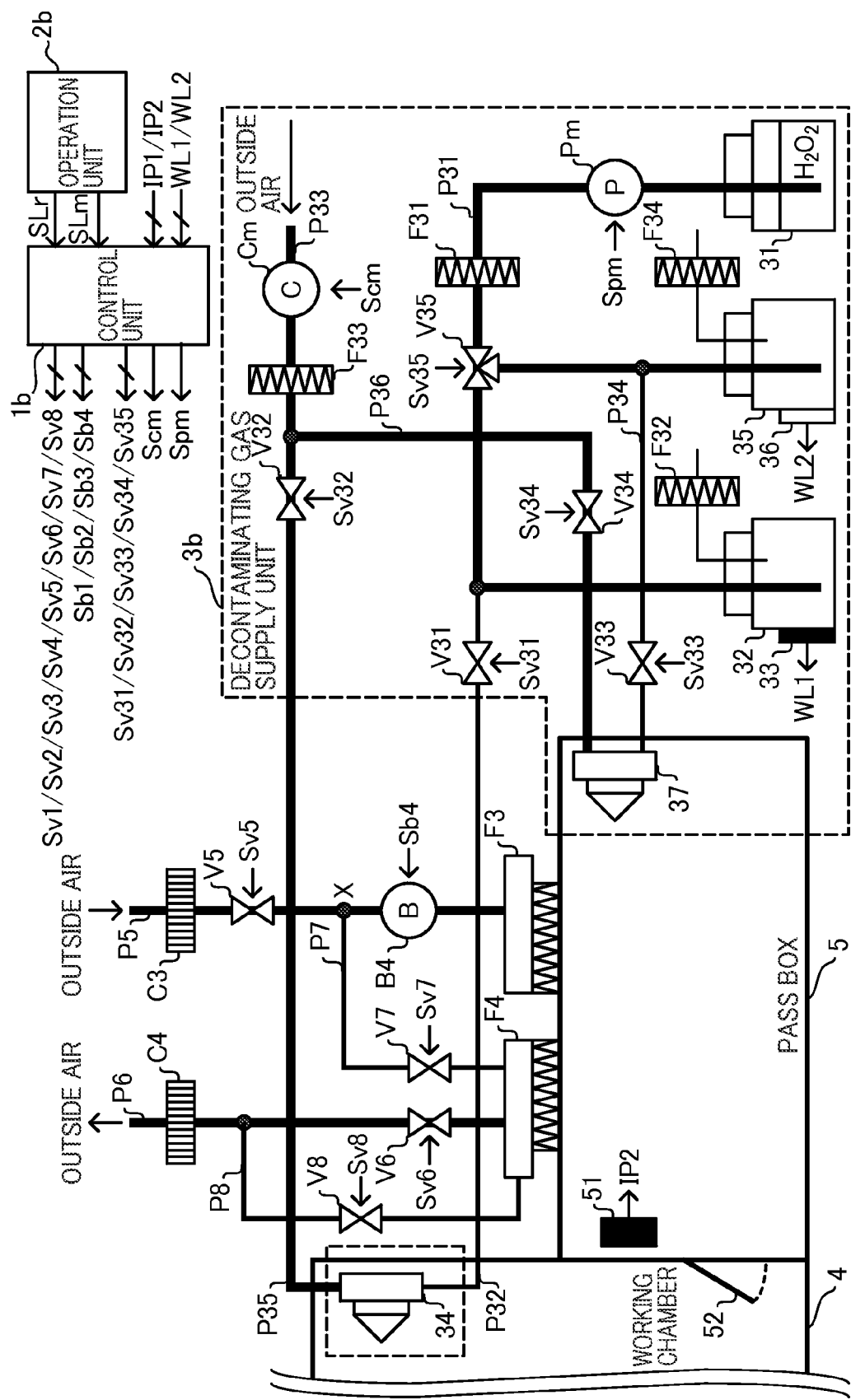
FIG. 7 is a block diagram illustrating another configuration example of an isolator.

In an embodiment described above, it was assumed that only the working chamber 4 is the chamber to be decontaminated, however, it is not limited thereto. For example, as illustrated in FIG. 7, a pass box 5 for bringing equipment necessary for the work into the working chamber 4 through a door 52 may be the chamber to be decontaminated, in addition to the working chamber 4. It should be noted that the components for decontaminating the working chamber 4 are similar to those in the isolator according to an embodiment described above, and thus are omitted in FIG. 7 except for the atomizer 34 and the like. Description of the components for decontaminating the working chamber 4, which are common to those in an embodiment described above, will hereinafter be omitted.

The isolator illustrated in FIG. 7 includes a control unit 1b, an operating unit 2b, and a decontaminating gas supply unit 3b. The pass box 5 includes an inlet provided with an (intake) filter F3 and an outlet provided with a (discharge) filter F4, and the inlet and outlet are provided with flow paths P5 to P8.

Further, the pass box 5 includes therein a pressure sensor 51 configured to measure the internal pressure IP2 of the pass box 5.

A (first) flow path P5 is a flow path for taking in the outside air to the pass box 5 through the filter F3, and a catalyst C3, a (first) valve V5, and a blower B4 are provided on the flow path P5. Whereas, a (second) flow path P6 is a flow path for discharging gas in the pass box 5 through the filter F4, and a catalyst C4 and a (second) valve V6 are provided on a flow path P6. The blower B4 is an axial-flow fan, for example, and is configured to produce air currents to take in the outside air to the pass box 5 through the flow path P5 as well as discharge the gas in the pass box 5 through the flow path P6, in response to a control signal Sb4. Since the capacity of the pass box 5 is smaller than that of the working chamber 4, such intake and discharge are performed by the a single blower B4.

By the air currents, the outside air flows in through the catalyst C3, and is further supplied into the pass box 5 through the filter F3, while the gas in the pass box 5 flows out through the filter F4, and furthermore the hydrogen peroxide is decomposed/rendered harmless by the catalyst C4, to be discharged to the exterior. The valve V5 is provided between the catalyst C3 and the blower B4, and is configured to open/close the flow path P5 in response to a control signal Sv5; while the valve V6 is provided between the catalyst C4 and the filter F4, and is configured to open/close the flow path P6 in response to a control signal Sv6.

One end of a flow path P7 is connected to a connection point x between the valve V5 and the blower B4 while the other end thereof is connected to the filter F4, and a (third) valve V7 is provided on the flow path P7. The valve V7 is configured to open/close the flow path P7 in response to a control signal Sv7.

In the isolator illustrated in FIG. 7, a flow path between the connection point x and the filter F3 in the first flow path P5, in combination with the flow path P7, corresponds to the third flow path. Further, the blower B4, which is provided on a flow path (flow path between the connection point x and the filter F3) common to the third flow path and the first flow path P5, serves both as the first blower for intake/discharge and the second blower for circulation. The blower B4 functions as the second blower in the decontaminating gas production mode and the decontaminating gas exposure mode, and functions as the first blower in the decontaminating gas discharge mode and the aseptic operation mode.

A (fourth) flow path P8 is another flow path, different from the flow path P6, for discharging the gas in the pass box 5 through the filter F4 in the decontaminating gas production mode and the decontaminating gas exposure mode. One end of the flow path P8 is connected to the flow path P6 between the catalyst C4 and the valve V6 while the other end thereof is connected to the filter F4, and a (fourth) valve V8 is provided on the flow path P8. The valve V8 is configured to open/close the flow path P8 in response to a control signal Sv8.

The decontaminating gas supply unit 3b includes the tank 31, the bottles 32 and 35, the water level sensors 33 and 36, the atomizers 34 and 37, and the filters F32 and F34, and further includes the flow paths P31 to P33 and flow paths P34 to P36 provided so as to connect the aforementioned components.

The flow path P31 connects between the tank 31 and the bottles 32 and 35; and the pump Pm, the filter F31, and a valve V35 are provided on the flow path P31. Further, the pump Pm is configured to take in the hydrogen peroxide solution stored in the tank 31 and deliver it toward the atomizers 34 and 37 through the filter F31, in response to the control signal Spm.

Further, the valve V35 allows the hydrogen peroxide solution filtered by the filter F31 to pass therethrough toward the atomizer 34 or the atomizer 37 in response to a control signal Sv35.

The bottle 32 is opened to the outside air through the (air) filter F32, and the bottle 32 is provided with the water level sensor 33 configured to measure the water level WL1 of the hydrogen peroxide solution. Whereas, the bottle 35 is opened to the outside air through the (air) filter F34, and the bottle 35 is provided with the water level sensor 36 configured to measure a water level WL2 of the hydrogen peroxide solution.

One end of the flow path P32 is connected to the flow path P31 between the valve V35 and the bottle 32 while the other end thereof is connected to the lower port of the atomizer 34, and the valve V31 is provided on the flow path P32. Whereas, one end of a flow path P34 is connected to the flow path P31 between the valve V35 and the bottle 35 while the other end thereof is connected to a lower port of the atomizer 37, and a valve V33 is provided on the flow path P34. The valve V31 is configured to open/close the flow path P32 in response to the control signal Sv31, and the valve V33 is configured to open/close the flow path P34 in response to a control signal Sv33.

The flow path P33 is a flow path for supplying compressed air to the atomizer 34 or 37, and is bifurcated into the flow path P35 connected to the atomizer 34 and a flow path P36 connected to the atomizer 37. The compressor Cm and the filter F33 are provided on the flow path P33, the valves V32 and V34 are provided on the flow paths P35 and P36, respectively. Further, the compressor Cm is configured to take in the outside air to be compressed in response to the control signal Scm, and such compressed air is supplied to the upper port of the atomizer 34 or the atomizer 37 through the (air) filter F33. The valve V32 is provided between the filter F33 and the upper port of the atomizer 34 and is configured to open/close the flow path P35 in response to the control signal Sv32, while the valve V34 is provided between the filter F33 and the upper port of the atomizer 37 and is configured to open/close the flow path P36 in response to a control signal Sv34.

From the operating unit 2b, a decontamination-target-chamber-selection signal SLr and the mode selection signal SLm are inputted to the control unit 1b. The control unit 1b is configured to select the working chamber 4 or the pass box 5 as the chamber to be decontaminated in response to the decontamination-target-chamber-selection signal SLr, and switch an operation mode in response to the mode selection signal SLm. Further, the control unit 1b is configured to output, in addition to selecting the chamber to be decontaminated and switching the operation mode, the control signals Sv1 to Sv6, Sv31 to Sv35, Sb1 to Sb3, Scm, and Spm based on the internal pressures IP1 and IP2 and the water levels WL1 and WL2. The decontaminating gas supply unit 3b is configured to supply the compressed air and the hydrogen peroxide gas into the chamber to be decontaminated selected in response to the decontamination-target-chamber-selection signal SLr.

Figure 8:
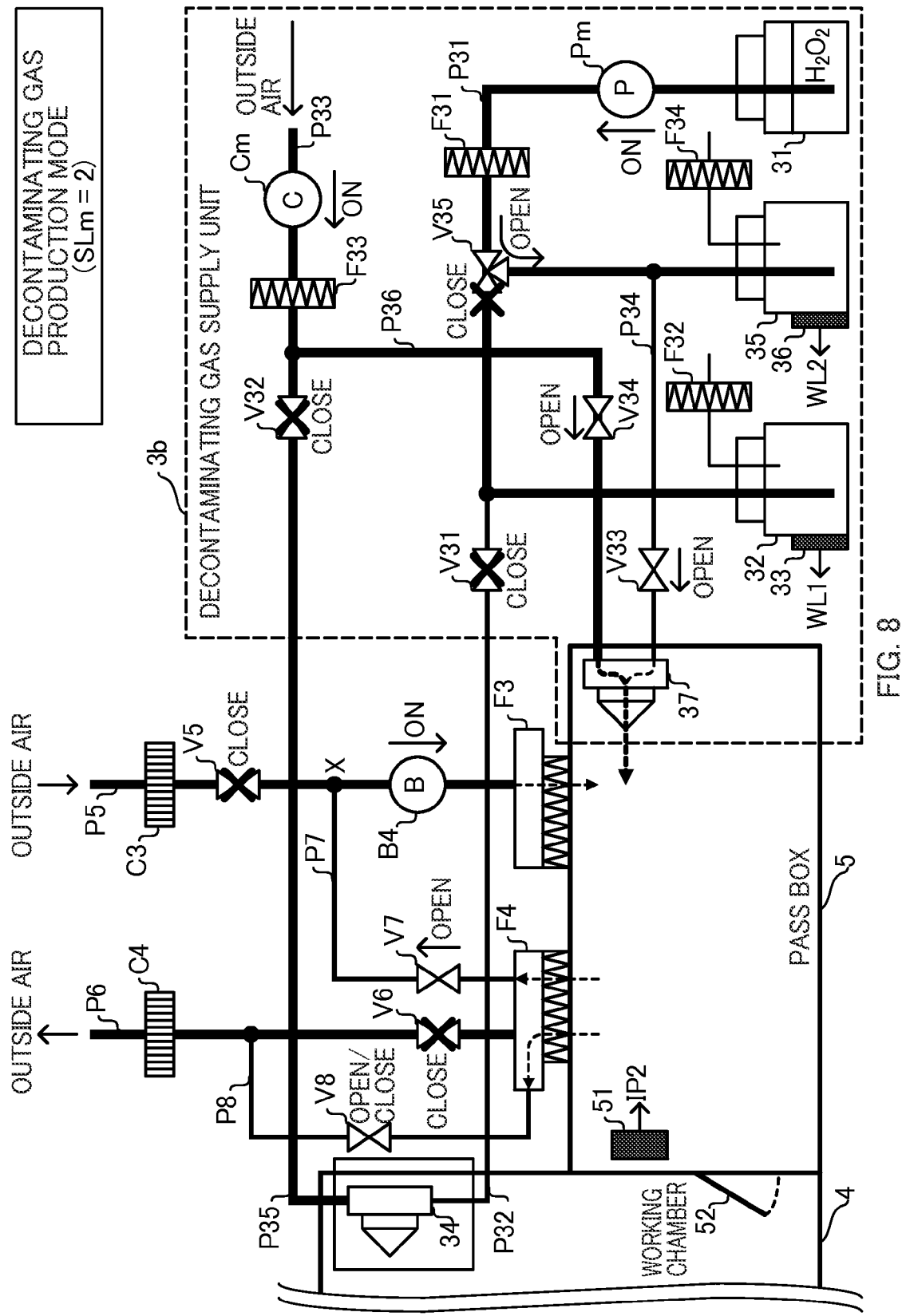
FIG. 8 is a block diagram illustrating state of valves, blowers, a compressor Cm, and a pump Pm in a decontaminating gas production mode in an isolator illustrated in FIG. 7.

In the isolator illustrated in FIG. 7, the operation mode is switched in response to the mode selection signal SLm, and the control is performed as in the isolator according to an embodiment described above. For example, in the decontaminating gas production mode with respect to the pass box 5, as illustrated in FIG. 8, the decontaminating gas supply unit 3b has the compressed air supplied to the upper port of the atomizer 37 and the hydrogen peroxide solution supplied to the lower port thereof by the negative pressure, to directly supply the hydrogen peroxide gas into the pass box 5. Further, the control unit 1b is configured to control opening/closing of the valve V8 based on the internal pressure IP2 of the pass box 5, so as to circulate the hydrogen peroxide gas in the pass box 5 by the blower B4 through the filters F3 and F4, and the third flow path while the internal pressure IP2 of the pass box 5 is being adjusted to the predetermined positive pressure IPtg.

Figure 9:
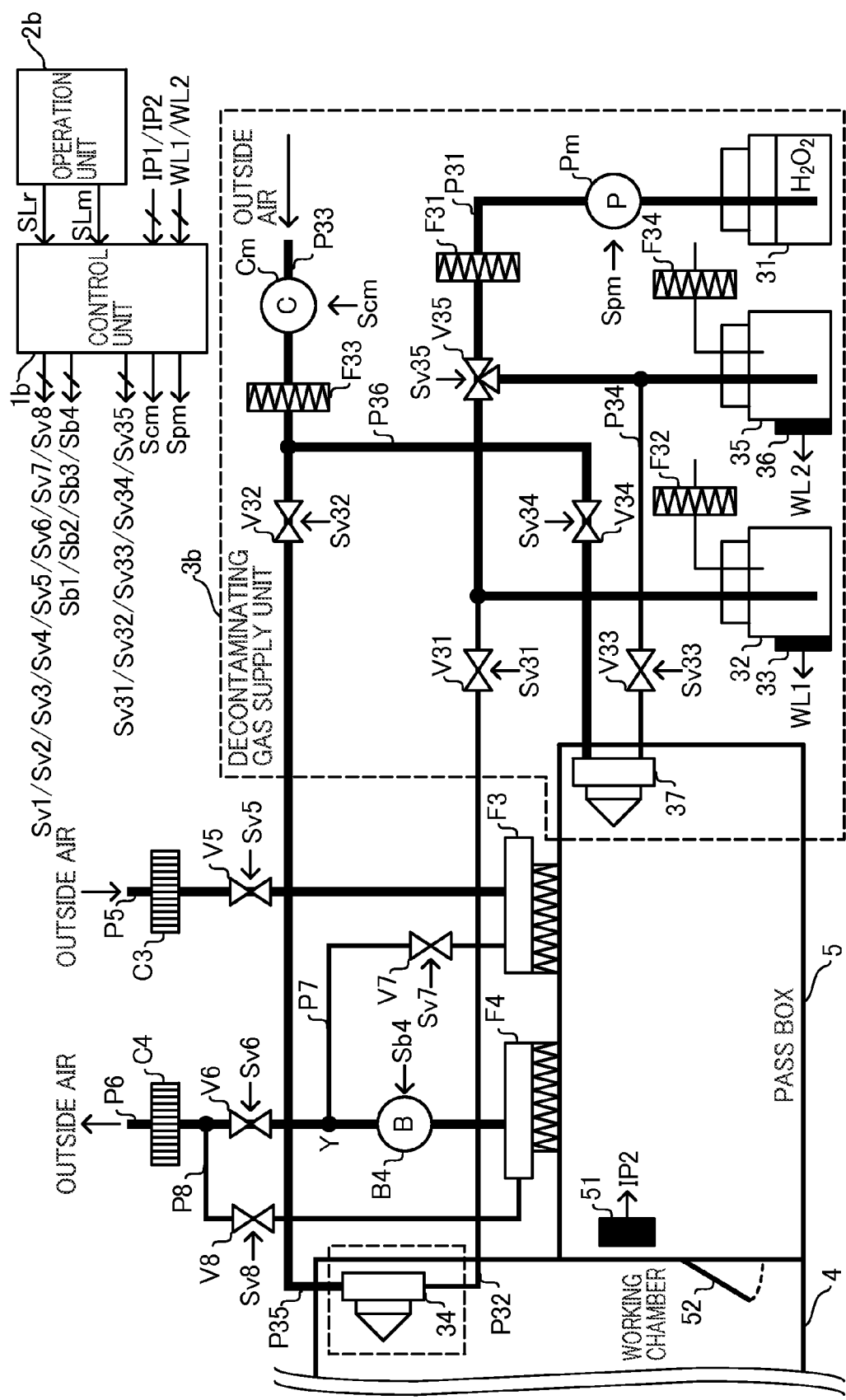
FIG. 9 is a block diagram illustrating yet another configuration example of an isolator.
Figure 10:
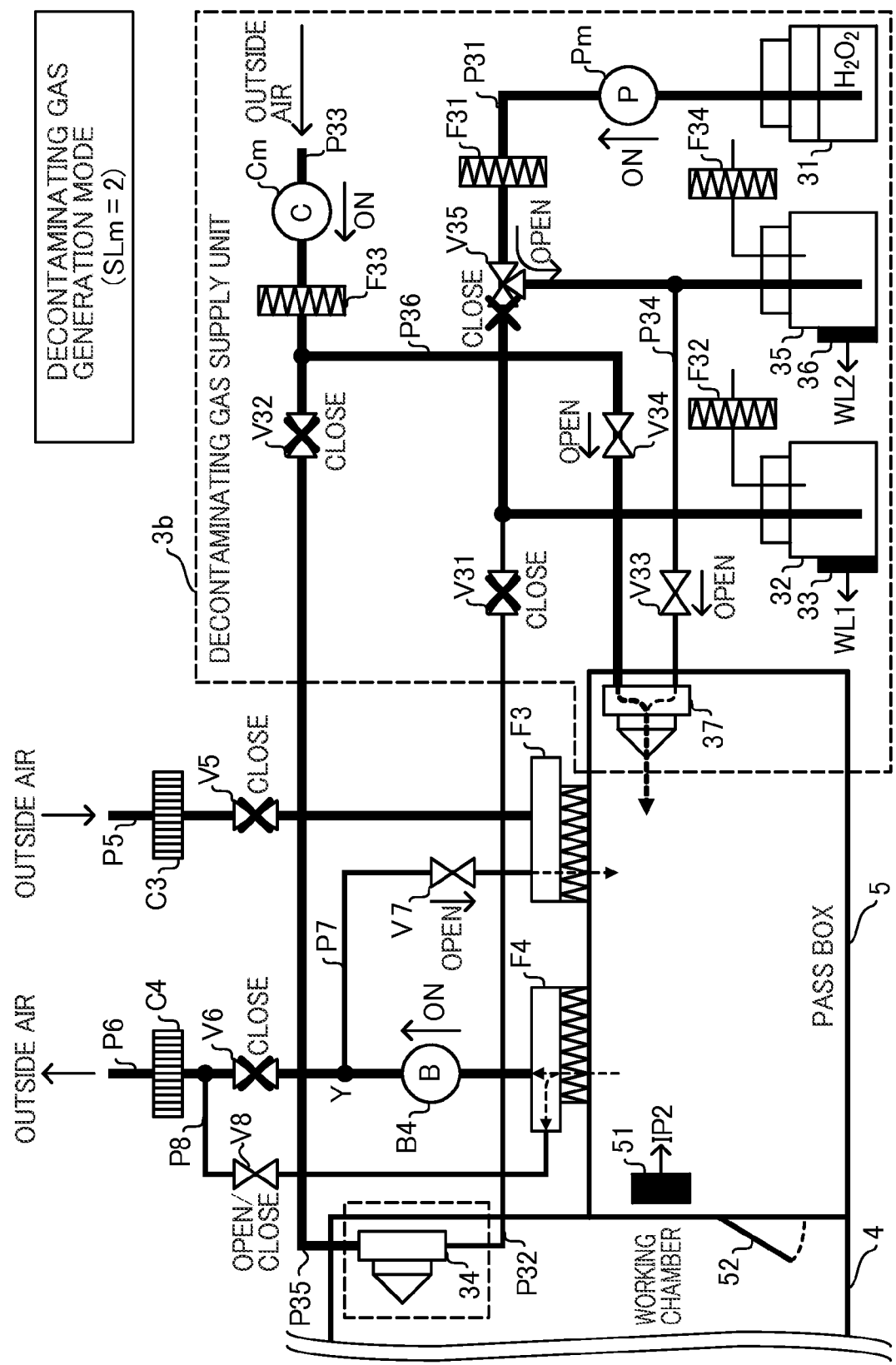
FIG. 10 is a block diagram illustrating a state of a valve, a blower, a compressor Cm, and a pump Pm in a decontaminating gas production mode in an isolator illustrated in FIG. 9.

In the isolator illustrated in FIG. 7, the third flow path and the flow path P5 includes a common flow path, and the blower B4 is provided on the common flow path, however, it is not limited thereto. For example, as illustrated in FIG. 9, a configuration may be such that the third flow path and the second flow path P6 includes a common flow path (flow path between a connection point Y and the filter F4), and the blower B4, which is provided on the common flow path, serves both as the first blower for intake/discharge and the second blower for circulation. As illustrated in FIG. 10, for example, the isolator with such a configuration also is controlled by a control signal similar to that in the isolator illustrated in FIG. 7.

As described above, in the decontaminating gas production mode of the isolator illustrated in FIG. 1 (FIG. 7, FIG. 9), The hydrogen peroxide gas, which is the decontaminating gas, is directly supplied into the working chamber 4 (pass box 5), which is the chamber to be decontaminated, without flowing through the filter F1 (F3), being the intake filter, and the filter F2 (F4), being the discharge filter, and the decontaminating gas in the chamber to be decontaminated is circulated through the intake filter, the discharge filter, and the third flow path P3 (P7 and common flow path) connecting the intake and discharge filters at the exterior of the chamber to be decontaminated, thereby supplying a sufficient amount of decontaminating gas into the chamber to be decontaminated, and further, sufficiently decontaminating not only the discharge filter but also the intake filter. Thus, the efficiency of the process of decontaminating the interior of the chamber to be decontaminated and the intake filter can be improved.

Further, in the decontaminating gas production mode, while the decontaminating gas is being supplied into the chamber to be decontaminated from the decontaminating gas supply unit 3a (3b), the second blower B3 (B4) is driven as well as the third flow path, which is opened/closed by the third valve V3 (V7), is opened, in a state where the first flow path P1 (P5) for performing intake and the second flow path P2 (P6) for performing discharge by the first blowers B1 and B2 (B4) are closed, thereby circulating the decontaminating gas in the chamber to be decontaminated through the intake filter, the discharge filter, and the third flow path, so that the intake filter can sufficiently be decontaminated.

Further, the catalyst C2 (C4) for decomposing the decontamination material is provided on the side more distant (away) from the discharge filter as compared with the second valve V2 (V6) configured to open/close the second flow path, one end of the fourth flow path P4 (P8) connected between the catalyst and the second valve, the other end thereof connected to the discharge filter, and opening/closing of the fourth valve V4 (V8), which is configured to control open/close the fourth flow path, is controlled based on the internal pressure IP1 (IP2) of the chamber to be decontaminated that is measured by the pressure sensor 41 (51) in the decontaminating gas production mode, thereby being able to circulate the decontaminating gas in the chamber to be decontaminated through the intake filter, the discharge filter, and the third flow path, while the internal pressure of the chamber to be decontaminated is being adjusted to the predetermined positive pressure IPtg. Further, with such connection, the decontamination material contained in the decontaminating gas, which is discharged not only in the decontaminating gas discharge mode and the aseptic operation mode but also the decontaminating gas production mode and the decontaminating gas exposure mode, is decomposed and rendered harmless, then to be discharged to the exterior.

Further, in the decontaminating gas production mode, the decontaminating gas is produced by mixing the compressed gas and the decontamination material, to be supplied into the chamber to be decontaminated; and thereafter, in the decontaminating gas exposure mode, while only the compressed gas is being supplied into the chamber to be decontaminated, the decontaminating gas in the chamber to be decontaminated is circulated as well as opening/closing of the fourth valve is controlled; thereby being able to sufficiently decontaminate the interior of the chamber to be decontaminated and the intake filter while suppressing the consumption of the decontamination material, as in the contamination gas production mode.

Further, only the compressed gas is supplied into the chamber to be decontaminated in a state where the first, second, and fourth valves are closed and the third valve opened, thereby being able to test the airtightness of the chamber to be decontaminated and the third flow path based on the internal pressure of the chamber to be decontaminated.

Further, in the isolator illustrated in FIGS. 7 and 9, the third flow path includes the flow path common to the first or the second flow path, and the second blower for circulation is provided on the flow path common thereto, so that the second blower serves also as the first blower for intake and discharge, that is to say, the second blower can be used as the second blower in the decontaminating gas production mode and the decontaminating gas exposure mode, while used as the first blower in the decontaminating gas discharge mode and the aseptic operation mode.

The above embodiments of the present invention are simply for facilitating the understanding of the present invention and are not in any way to be construed as limiting the present invention. The present invention may variously be changed or altered without departing from its spirit and encompass equivalents thereof.

What is claimed is:

1. An isolator comprising:
a chamber to be decontaminated including an inlet provided with an intake filter and an outlet provided with a discharge filter;
a first flow path through which outside air is taken into the chamber to be decontaminated via the intake filter;
a second flow path through which gas in the chamber to be decontaminated is discharged via the discharge filter;
a first blower provided on the first flow path to take in the outside air to the chamber to be decontaminated through the first flow path;
a second blower provided on the second flow path to discharge the gas in the chamber to be decontaminated through the second flow path;
a decontaminating gas supply unit configured to supply decontaminating gas into the chamber to be decontaminated without flowing through the intake filter and the discharge filter;
a third flow path configured to connect the intake filter and the discharge filter at an exterior of the chamber to be decontaminated; and
a third blower provided on the third flow path to circulate the gas in the chamber to be decontaminated through the intake filter, the third flow path, and the discharge filter, in this order,
wherein the first blower and the second blower are not provided on the third flow path,
wherein the decontaminating gas supply unit, includes
an atomizer including a first port, a second port, and a nozzle,
a first pipe having a first end connected to an air compressor and having a second end connected to the first port,
a second pipe connected to the second port, the second pipe having a first end connected to the second port and having a second end which is open, the first port being positioned higher than the second port, and the nozzle being disposed at a position vertically between the first port and the second port,
a reservoir portion configured to store decontamination solution,
a pump configured to take in decontamination solution from the reservoir portion, and
a third pipe, having a first end connected to the pump, through which the decontamination solution taken in by the pump flows, and
wherein the atomizer is configured to, when injecting from the nozzle air taken in from the first port, suction decontamination solution flowing through the third pipe, via the second pipe, by the negative pressure produced in the second port; and inject the decontamination solution in an atomized state from the nozzle, mixing the decontamination solution with air.

2. The isolator according to claim 1 further comprising:
a first valve configured to open/close the first flow path;
a second valve configured to open/close the second flow path; and
a third valve configured to open/close the third flow path;
wherein, in a case where the decontaminating gas is supplied into the chamber to be decontaminated, the third blower is driven, the third valve is opened, and the first and second valves are closed, so that the gas in the chamber to be decontaminated is circulated.

3. The isolator according to claim 2 further comprising:
a fourth flow path through which the gas in the chamber to be decontaminated is discharged via the discharge filter;
a fourth valve configured to open/close the fourth flow path;
a detoxifying unit provided on the second flow path, the detoxifying unit configured to reduce an amount of a decontamination material contained in the decontaminating gas, to be rendered harmless;
a pressure sensor configured to measure an internal pressure of the chamber to be decontaminated,
wherein the second valve is provided between the detoxifying unit and the discharge filter,
wherein the fourth flow path is configured to connect the discharge filter and a flow path, in the second flow path, between the detoxifying unit and the second valve, and
wherein, in a case where the decontaminating gas is supplied into the chamber to be decontaminated, the fourth valve is opened/closed based on a measurement result of the pressure sensor, so that the gas in the chamber to be decontaminated is circulated while the internal pressure of the chamber to be decontaminated is adjusted to a predetermined positive pressure.

4. The isolator according to claim 3,
wherein the decontaminating gas supply unit includes a compressor configured to supply compressed gas, and an atomizer configured to produce the decontaminating gas by mixing the compressed gas and the decontamination material, wherein the decontaminating gas supply unit is configured to, after supplying the decontaminating gas into the chamber to be decontaminated, supply only the compressed gas thereinto, and wherein in a case where, after the decontaminating gas is supplied into the chamber to be decontaminated, only the compressed gas is supplied thereinto, gas is circulated in the chamber to be decontaminated while the internal pressure of the chamber to be decontaminated is adjusted to the predetermined positive pressure.

5. The isolator according to claim 4, wherein the first, second and fourth valves are closeable and the third valve is openable, and wherein the decontaminating gas supply unit is configured to supply only the compressed gas into the chamber to be decontaminated, in a case where airtightness of the chamber to be decontaminated is tested based on the internal pressure of the chamber to be decontaminated measured by the pressure sensor.

6. An isolator comprising:

a chamber to be decontaminated including an inlet provided with an intake filter and an outlet provided with a discharge filter;

a first flow path through which outside air is taken into the chamber to be decontaminated via the intake filter;

a second flow path through which gas in the chamber to be decontaminated is discharged via the discharge filter;

a first blower provided on the first flow path to take in the outside air to the chamber to be decontaminated through the first flow path;

a second blower provided on the second flow path to discharge the gas in the chamber to be decontaminated through the second flow path;

a decontaminating gas supply unit configured to supply decontaminating gas into the chamber to be decontaminated without flowing through the intake filter and the discharge filter;

a third flow path configured to connect the intake filter and the discharge filter at an exterior of the chamber to be decontaminated; and a third blower provided on the third flow path to circulate the gas in the chamber to be decontaminated through the intake filter, the third flow path, and the discharge filter, in this order, wherein the first blower and the second blower are not provided on the third flow path, wherein the decontaminating gas supply unit, includes an atomizer including a first port, a second port, and a nozzle, a reservoir portion configured to store decontamination solution, a pump configured to take in decontamination solution from the reservoir portion, a first pipe having a first end connected to an air compressor and having a second end connected to the first port, a second pipe having a first end connected to the second port and having a second end, the first port being positioned higher than the second port, and the nozzle being disposed at a position vertically between the first port and the second port, and a third pipe having a first end connected to the pump and having a second end which is open, wherein the second end of the second pipe is connected to the third pipe between the first end and the second end of the third pipe, wherein the atomizer configured to inject the decontamination solution with air in an atomized state from the nozzle, when injecting from the nozzle air taken in from the first port, a negative pressure produced in the second port, the decontamination solution flowing through the third pipe suctioned by the negative pressure via the second pipe, and wherein a flow-path diameter of the second pipe is smaller than a flow-path diameter of the third pipe.

7. The isolator according to claim 6, further comprising:

a first valve configured to open/close the first flow path;

a second valve configured to open/close the second flow path; and a third valve configured to open/close the third flow path;

wherein, in a case where the decontaminating gas is supplied into the chamber to be decontaminated, the third blower is driven, the third valve is opened, and the first and second valves are closed, so that the gas in the chamber to be decontaminated is circulated.

8. The isolator according to claim 7, further comprising:

a fourth flow path through which the gas in the chamber to be decontaminated is discharged via the discharge filter;

a fourth valve configured to open/close the fourth flow path;

a detoxifying unit provided on the second flow path, the detoxifying unit configured to reduce an amount of a decontamination material contained in the decontaminating gas, to be rendered harmless;

a pressure sensor configured to measure an internal pressure of the chamber to be decontaminated, wherein the second valve is provided between the detoxifying unit and the discharge filter, wherein the fourth flow path is configured to connect the discharge filter and a flow path, in the second flow path, between the detoxifying unit and the second valve, and wherein, in a case where the decontaminating gas is supplied into the chamber to be decontaminated, the fourth valve is opened/closed based on a measurement result of the pressure sensor, so that the gas in the chamber to be decontaminated is circulated while the internal pressure of the chamber to be decontaminated is adjusted to a predetermined positive pressure.

9. The isolator according to claim 8, wherein the decontaminating gas supply unit includes a compressor configured to supply compressed gas, and an atomizer configured to produce the decontaminating gas by mixing the compressed gas and the decontamination material, wherein the decontaminating gas supply unit is configured to, after supplying the decontaminating gas into the chamber to be decontaminated, supply only the compressed gas thereinto, and wherein in a case where, after the decontaminating gas is supplied into the chamber to be decontaminated, only the compressed gas is supplied thereinto, gas is circulated in the chamber to be decontaminated while the internal pressure of the chamber to be decontaminated is adjusted to the predetermined positive pressure.

10. The isolator according to claim 9, wherein wherein the first, second and fourth valves are closeable and the third valve is openable, and wherein the decontaminating gas supply unit is configured to supply only the compressed gas into the chamber to be decontaminated, in a case where airtightness of the chamber to be decontaminated is tested based on the internal pressure of the chamber to be decontaminated measured by the pressure sensor.

* * * * *